United States Patent [19]

Fino et al.

[11] Patent Number: 4,476,229
[45] Date of Patent: Oct. 9, 1984

[54] SUBSTITUTED CARBOXYFLUORESCEINS

[75] Inventors: James R. Fino, Vernon Hills; Curtis L. Kirkemo, Gurnee, both of Ill.

[73] Assignee: Abbott Laboratories, North Chicago, Ill.

[21] Appl. No.: 440,067

[22] Filed: Nov. 8, 1982

[51] Int. Cl.$^3$ .............. G01N 33/52; C07D 311/82
[52] U.S. Cl. .................... 436/500; 436/537; 436/546; 436/800; 549/223
[58] Field of Search ............ 436/500, 537, 546, 800; 549/223

[56] References Cited

U.S. PATENT DOCUMENTS

| | | | |
|---|---|---|---|
| 4,161,515 | 7/1979 | Ullman | 424/8 |
| 4,347,058 | 8/1982 | Polito et al. | 436/500 |
| 4,347,059 | 8/1982 | Polito et al. | 436/500 |

FOREIGN PATENT DOCUMENTS

| | | | |
|---|---|---|---|
| 0015695 | 9/1980 | European Pat. Off. | 436/500 |
| 3205506 | 9/1982 | Fed. Rep. of Germany | 436/500 |
| 2487835 | 2/1982 | France | 436/500 |

OTHER PUBLICATIONS

Maratsugu et al., Chem. Abstracts, vol. 97, (1982), #175226h.

*Primary Examiner*—Christine M. Nucker
*Attorney, Agent, or Firm*—Dennis K. Shelton

[57] ABSTRACT

This disclosure relates to a method and reagents for determining ligands in biological fluids such as serum, plasma, spinal fluid, amnionic fluid and urine. This disclosure also relates to a novel class of tracer compounds employed as reagents in fluorescence polarization immunoassays.

11 Claims, No Drawings

SUBSTITUTED CARBOXYFLUORESCEINS

BACKGROUND OF THE INVENTION

The present invention relates to a method and reagents for determining ligands in biological fluids such as serum, plasma, spinal fluid, amnionic fluid and urine. The present invention also relates to a novel class of fluorescein derivatives which may be employed as reagents in fluorescent polarization immunoassays.

Competitive binding immunoassays for measuring ligands are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitively measured and is inversely proportional to the quantity of ligand in the test sample. Fluorescence polarization techniques are based on the principle that a fluorescent labeled compound when excited by lineraly polarized light will emit fluorescence having a degree of polarization inversely related to its rate of rotation. Therefore, when a molecule such as a tracer-antibody conjugate having a fluorescent label is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescence polarization provides a quantitive means for measuring the amount of tracer-antibody conjugate produced in a competitive binding immunoassay.

Various fluorescent labeled compounds are known in the art. U.S. Pat. No. 3,998,943 describes the preparation of a fluorescently labeled insulin derivative using fluorescein isothiocyanate (FITC) as the fluorescent label and a fluorescently labeled morphine derivative using 4-aminofluorescein hydrochloride as the fluorescent label. Carboxyfluorescein has also been used for analytical determinations. R. C. Chen, Analytical Letters, 10, 787 (1977) describes the use of carboxyfluorescein to indicate the activity of phospholipase. The carboxyfluorescein as described is encapsulated in lecithin liposomes, and it will fluoresce only when released by the hydrolysis of lecithin. U.S. application Ser. No. 329,974, filed Dec. 11, 1981, discloses a class of carboxyfluorescein derivatives useful as reagents in fluorescent polarization immunoassays wherein the carboxyfluorescein is directly bonded to a ligand-analog.

SUMMARY OF THE INVENTION

The present invention encompasses a method for determining ligands in a sample comprising intermixing with said sample a biologically acceptable salt of a tracer of the formula:

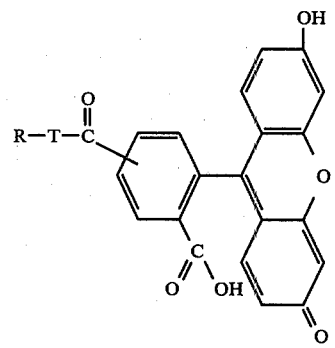

T is a

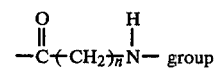

wherein n is an integer of from 1 to 8; and
wherein
R is a ligand-analog having a reactive primary or secondary amino group which is attached to the carbonyl carbon of the group represented by T wherein said ligand-analog has at least one common epitope with said ligand so as to be specifically reconizable by a common antibody;
and an antibody capable of specifically recognizing said ligand and said tracer; and then determining the amount of tracer antibody conjugate by fluorescence polarization techniques as a measure of the concentration of said ligand in the sample.

The invention further relates to certain novel tracers and biologically acceptable salts thereof, which are useful in reagents in the above-described method.

DETAILED DESCRIPTION OF THE INVENTION

The term "ligand" as used herein refers to a molecule, in particular a low molecular weight hapten having a single reactive amino group, to which a binding protein, normally an antibody, can be obtained or formed. Such haptens are protein-free compounds, generally of low molecular weight that do not include antibody formation when injected into an animal, but are reactive to antibodies. Antibodies to haptens are generally raised by first conjugating the haptens to a protein and injecting the conjugate product into an animal. The resulting antibodies are isolated by conventional antibody isolation techniques.

Ligands determinable by the method of the present invention vary over a wide molecular weight range. Although high molecular weight ligands may be determined, for best results, it is genrally preferable to employ the methods of the present invention to determine ligands of low molecular weight, generally in a range of 50 to 4000. It is more preferred to determine ligands having a molecular weight in a range of 100 to 2000.

Representative of ligands determinable by the methods of the present invention include steroids such as estriol estrone, estradiol, cortisol, testostrone, progesterone, deoxycholic acid, lithocholic acid and the ester and amide derivatives thereof; vitamins such as B-12, folic acid; thyroxine, triiodothyronine, histamine, serotonin, prostaglandins such as PGE, PGF, PGA; antiasthamatic drugs such as theophylline, antineoplastic drugs such as doxorubicin and methotrexate; antiarrhythmic drugs such as disopyramide, lidocaine, procainamide, propranolol, quinidine, N-acetyl-procainamide; anticonvulsant drugs such as phenobarbital, phenytion, primidone, valproic acid, carbamazepine and ethosuximide; antibiotics such as penicillins, cephalosporins and vancoymcin; antiarthritic drugs such as salicylates; antidepressent drugs including tricyclics such as nortriptyline, amitriptyline, imipramine and desipramine; and the like as well as the metabolites thereof. Additional ligands that may be determined by the methods of the present invention include drugs of abuse such as morphine, heroin, hydromorphone, oxymorphone, metapon, codeine, hydrocodone, dihydrocodeine, dihydrohydroxycodeinone, pholcodine, dextromethorphan, phenazocine and deonin and their metabolites.

The term ligand-analog as used herein refers to a mono or polyvalent radical a substantial portion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand analog will have the same or substantially the same structure and charge distribution (spatial and polar organization) as the ligand of interest for a significant portion of the molecular surface. Since frequently, the linking site for a hapten will be the same in preparing the antigen for production of antibodies as used for linking to the ligand, the same portion of the ligand analog which provides the template for the antibody will be exposed by the ligand analog in the tracer.

In general, the class of ligand analogs represented by R are derived from the corresponding ligand by removal of a hydrogen atom, bonded to a reactive amine (primary or secondary) or by the formation of an amino derivative of the ligand wherein an amino group

replaces one or more atoms originally present in the ligand, at the site of binding to the carbonyl carbon in the groups represented by T. Illustrative of ligands which upon the removal of a hydrogen from an active amino group may form ligand-analogs represented by R include for example, procainamide, thyroxine and quinidine. Illustrative of ligands whose amino derivatives are useful as ligand-analog include theophylline, valproic acid, phenobarbital, phenytoin, primidone, disopyramide, digoxin, chloramphenicol, salicylate, acetaminophen, carbamazepine, desipramine and nortriptyline. In addition, a ligand may be structurally modified by the addition or deletion of one or more functional groups to form a ligand-analog, which retaining the necessary epitope sites for binding to an antibody. However, such modified ligand-analogs are bonded to the carbonyl carbon of the groups represented by T through an imino group.

It is preferred that in the groups represented by T, n is in a range of from 2 to 4.

The tracers of the present invention generally exist in an equilibrium between their acid and ionized states, and in the ionized state are effective in the method of the present invention. Therefore, the present invention comprises the tracers in either the acid or ionized state and for convenience, the tracers of the present in their ionized state, the tracers exist in the form of biologically acceptable salts. As used herein, the term "biologically acceptable salts" refers to salts such as sodium, potassium, ammonium and the like which will enable the tracers of the present invention to exist in their ionized state when employed in the method of the present invention. Generally, the tracers of the present invention exist in solution as salts, the specific salt results from the buffer employed, i.e., in the presence of a sodium phosphate buffer, the tracer of the present invention will generally exist in their ionized state as a sodium salt.

In accordance with the method of the present invention, a sample containing the ligand to be determined is intermixed with a biologically acceptable salt of a tracer of formula (I) and an antibody specific for the ligand and tracer. The ligand present in the sample and the tracer compete for limiting antibody sites resulting in the formation of ligand-antibody and tracer-antibody complexes. By maintaining constant the concentration of tracer and antibody, the ratio of ligand-antibody complex to tracer-antibody complex that is formed is directly proportional to the amount of ligand present in the sample. Therefore, upon exciting the mixture with polarized light and measuring the polarization of the fluorescence emitted by a tracer and a tracer-antibody complex, one is able to quantitatively determine the amount of ligand in the sample.

In theory, the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertical component of the emitted light, the polarization of fluorescence in the reaction mix may be accurately determined. The precise relationship between polarization and concentration of the ligand to be determined is established by measuring the polarization values of calibrators with known concentrations. The concentration of the ligand can be extrapolated from a standard curve prepared in this manner.

The pH at which the method of the present invention is practiced must be sufficient to allow the tracers of formula (I) to exist in their ionized state. The pH may range from about 3 to 12, more usually in the range of form about 5 to 10, most preferably from about 6 to 9. Various buffers may be used to achieve and maintain the pH during the assay procedure. Representation buffers include borate, phosphate, carbonate, tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about 0° to 50° C., more usually from about 15° to 40° C.

The concentration of ligand which may be assayed will generally vary from about $10^{-2}$ to $10^{-13}$M, more usually from about $10^{-4}$ to $10^{-10}$M. High concentrations of ligand may be assayed upon dilution of the original sample.

In addition to the concentration range of ligand of interest, considerations such as whether the assay is qualitative, semiquantitative or quantitative, the equipment employed, and the characteristics of the tracer and antibody will normally determine the concentration of the tracer and antibody to be employed. While the concentration of ligand in the sample will determine the range of concentration of the other reagents, i.e., tracer and antibody, normally to optimize the sensitivity of the assay, individual reagent concentrations will be determined empirically. Concentrations of the tracer and antibody are readily ascertained by one of ordinary skill in the art.

The preferred tracers of the present invention are characterized as derivatives of 5-carboxyfluorescein or 6-carboxyfluorescein or mixtures thereof and are represented by the formulas:

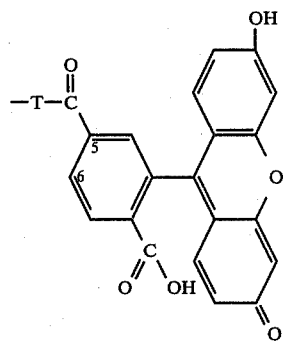

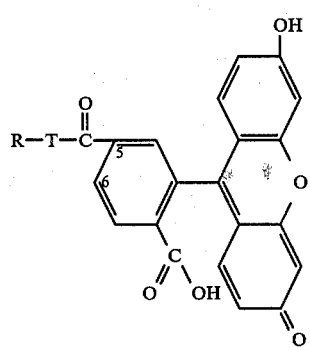

The following illustrative, nonlimiting examples will serve to further demonstrate to those skilled in the art the manner in which specific tracers within the scope of this invention may be prepared. The symbol [CF] appearing in the structural formulas illustrating the compounds prepared in the following examples, represents a moiety of the formula:

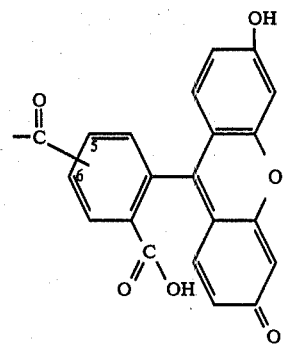

wherein the carbonyl carbon is attached to the 5 or 6 position depending on whether the starting material employed in the Example is 5-carboxyfluorescein, 6-carboxyfluorescein or a mixture thereof.

EXAMPLE 1

Preparation of N-Hydroxysuccinimide Active Ester of Carboxyfluorescein

To 83 mg (0.22 mmol) of 6-carboxyfluorescein dissolved in 2 ml of dimethylformamide was added 28 mg (0.24 mmol) of N-hydroxysuccinimide and 55 mg (0.27 mmol) of N,N'-dicyclohexylcarbodiimide. The reaction mixture was stirred at 0° C. under argon atmosphere for one hour and then maintained at 4° C. for 16 hours to yield a N-hydroxysuccinimide active ester of carboxyfluorescein having the formula:

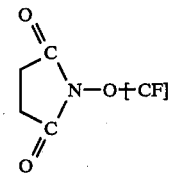

EXAMPLE 2

To a solution containing 5-aminovaleric acid (5.85 g, 0.05 mol) in 100 ml of 2% aqueous sodium hydroxide and 100 ml of dioxane was dropwise added a solution containing di-t-butyldicarbonate (10.9 g, 0.05 mol) in 40 ml of dioxane. The reaction mixture was stirred for 18 hours and then acidified to pH 3 using 1N hydrochloric acid. The acidified mixture was extracted three times with dichloromethane. The organic layers were combined, washed with water, and dried over sodium sulfate to yield 10.1 g (93.5% yield) of 5-(t-butoxycarbonylamino)valeric acid as a white crystalline solid.

To a portion of 5-(t-butoxycarbonylamino)valeric acid (0.434 g, 0.002 mol) was added N,N'-dicyclohexylcarbodiimide (0.412 g, 0.002 mol) and N-hydroxysuccinimide (0.25 g, 0.0022 mol) in 3 ml dichloromethane with constant stirring and the reaction was allowed to proceed for 18 hours to yield the N-hydroxysuccinimide active ester of 5-(t-butoxycarbonylamino)-valeric acid as an oily residue. To the oily residue was added L-thyroxine sodium salt pentahydrate (1.95 g, 0.0022 mol) in 30 ml of methanol.

The reaction was allowed to proceed for 18 hours after which time the reaction mixture was passed through an ion exchange resin column (Bio-Rad AG ® 50W-X8 (H+ form) using methanol as the eluent.

The eluent was concentrated under vacuum to yield 1.96 g (90% yield) of intermediate of the formula:

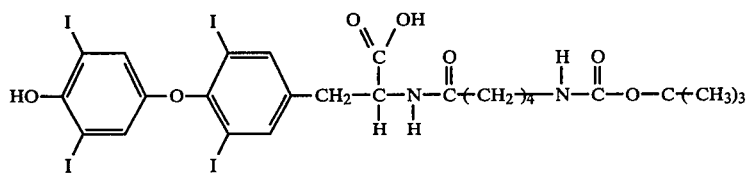

A portion of the intermediate (0.125 g, 0.00015 mol) was treated with trifluoroacetic acid (2.0 ml) for 30 minutes. The trifluoroacetic acid was removed via evaporation under reduced pressure and the resulting residue was dissolved in 1.5 ml of N,N'-dimethylformamide. The resulting solution was adjusted to a basic pH using triethylamine. To the resulting mixture was added N-hydroxysuccinimide active ester of carboxyfluorescein (75 mg, 0.000159 mol). The reaction was allowed to proceed for 18 hours. Diethylether was added to the reaction mixture to yield a precipitate which was purified via preparatory reverse phase TLC using a mixture of methanol:water:acetic acid (75:25:0.5) to yield 0.071 g of a thyroxine-6-carboxyfluorescein conjugate as an orange solid, having the formula:

Compound 1

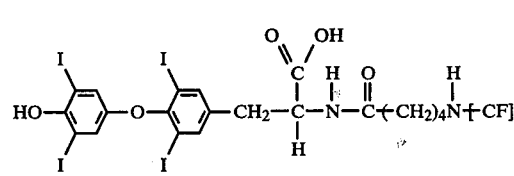

EXAMPLE 3

To a solution containing 10 g of β-alanine (0.1122 mol) in 100 ml of a 1:1 mixture of dioxane:water conatining 4.5 g (0.1125 mol) of sodium hydroxide was added dropwise a solution containing di-t-butydicarbonate (26.95 g:0.1235 mol) in 40 ml of dioxane. The reaction mixture was stirred for 16 hours and then acidified to pH 3 using 1N hydrochloric acid. The acidified mixture was extracted three times with dichloromethane. The organic layers were combined, washed with dilute hydrochloric acid and dried over magnesium sulfate to yield 17 g (93.5% yield) of 3-t-butoxycarbonylamino)propionic acid.

To a portion of 3-(t-butoxycarbonylamino)propionic acid (2.1 g:0.010 mol) dissolved in 25 ml of methylene chloride was added N,N'-dicyclohexylcarbodiimide (1.34 g:0.0116 mol) and N-hydroxysuccinimide (2.62 g:0.0127 mol). The reaction was allowed to proceed for 20 hours at room temperature under an argon atmosphere to yield an oily residue. The oily residue was redissolved in methylene chloride and the resulting solution was filtered. The filtrate was concentrated under vacuum to yield the N-hydroxysuccinimide active ester of 3-(t-butoxycarbonylamino)-propionic acid as a white solid.

A portion of the N-hydroxysuccinimide active ester of 3-(t-butoxycarbonylamino)propionic acid (0.24 g:0.0008 mol) was added to a solution containing L-thyroxine sodium salt pentahydrate (0.5 g:0.0006 mol) in 2 ml of methanol. As the reaction proceeded, a residue formed and with completion of the reaction, the residue was dissolved upon the addition of 1N sodium hydroxide. The reaction product was purified using a silica gel column using a 1:4 mixture of methanol:methylene chloride as the eluent. The eluent was concentrated to yield an intermediate of the formula:

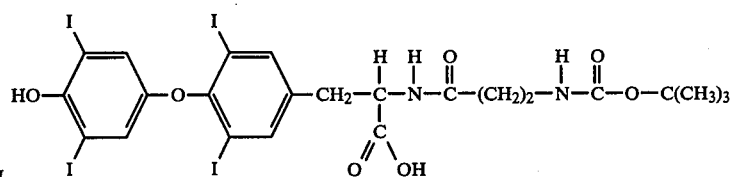

A portion of the intermediate (0.2 g:0.00021 mol) was dissolved in a saturated solution of dioxane containing hydrogen chloride and the resulting solution was stirred at room temperature for 2 hours. The dioxane:hydrochloric acid was removed under vacuum and the resulting residue was dissolved in 1.5 ml of N,N'-dimethylformamide. The resulting solution was adjusted to a neutral pH using triethylamine. To the resulting mixture was added succinimide active ester of 6-carboxyfluorescein (107 mg:0.00022 mol). The reaction was allowed to proceed for 16 hours under an argon atmosphere to yield a crude product which was purified via preparatory reverse phase thin-layer chromatography using a mixture of methanol:water:acetic acid (70:30:0.4) to yield 10.0 mg (4% yield of a thyroxine-6-carboxyfluorescein conjugate having the formula:

Compound 2

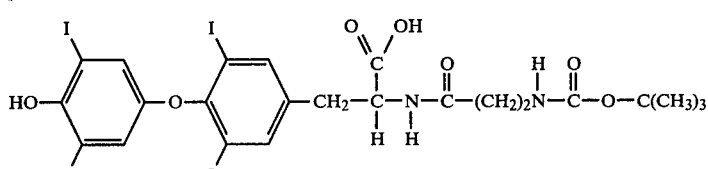

EXAMPLE 4

To a solution containing 6-aminocaproic acid (10g:0.07623 mmol) was added with constant stirring to a mixture containing 200 ml of a 1:1 of dioxane:water containing sodium hydroxide (3.05 g:0.07625 mmol). To the resulting solution was dropwise added di-t-butyldicarbonate (16.54 g:0.07623 mol) that has been diluted with 80 ml of dioxane. The reaction mixture was stirred for 16 hours and then acidified to pH 3 using 1N hydrochloric acid. The acidified mixture was extracted three times with dichloromethane. The organic layers were combined, concentrated under vacuum and the residue was dissolved in methylene chloride and then washed with diluted hydrochloric acid. The methylene chloride solution is then extracted with saturated sodium bicarbonate, saving the aqueous layer. The aqueous layers are adjusted to pH 3 using 1N hydrochloric acid and then extracted with methylene chloride. The methylene chloride extracts are dried with magnesium sulfate and concentrated under vacuum to yield 13 g (75% yield) of 5-(t-butoxycarbonylamino)caproic acid.

To a portion of the 5-t-butoxycarbonylamino(caproic acid) (1.0 g:0.00432 mol) dissolved in 10 ml of a 1:1 mixture of methylene chloride:dimethylformamide at room temperature under argon atmosphere. To the resulting solution was added N-hydroxysuccinimide (0.55 g:0.00478 mol) and then N,N'-dicyclohexylcarbodiimide (1.07 g:0.00519 mol). The reaction was allowed to proceed for twenty hours after which time the reaction mixture was filtered through Celite ® and the filtrate was concentrated to yield a residue which was redissolved in methylene chloride. The methylene chloride solution was filtered and concentrated to yield a white solid. To a solution containing L-thyroxine sodium salt pentahydrate (0.5 g:0.00056 mol) in 4 ml of methanol was added a portion of the white solid (0.58 g:0.00177 mol). The reaction mixture was stirred at room temperature under argon atmosphere for three hours and then concentrated to yield an intermediate as a tan powder having the following formula:

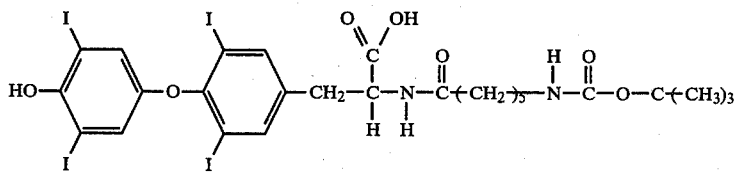

The portion of the intermediate (0.10 g:0.0001 mol) was dissolved in a 1:1 mixture of methylene chloride:trifluoroacetic acid at 0° C. under an argon atmosphere. After 45 minutes, the methylene chloride and trifluoroacetic acid were removed under vacuum to yield a residue which was then dissolved in 1 ml of dimethylformamide and the resulting solution was adjusted to pH 8 using triethylamine. The resulting solution was added to a solution containing 6-carboxyfluoroscein imidizolide which is prepared by reacting 6-carboxyfluorescein (0.38 g:0.0001 mol) dissolved in 1 ml of dimethylformamide with 1,1'-carbonyldiimidizole (0.016 g:0.0001 mol). The reaction mixture was stirred at room temperature under an argon atmosphere for four hours to yield a crude product which was purified using reverse phase thin-layer chromatography employing methanol:water:acetic acid (70:30:0.4) to yield 0.054 g (43% yield) of a thyroxine-6-carboxyfluorescein conjugate having the formula:

Compound 3

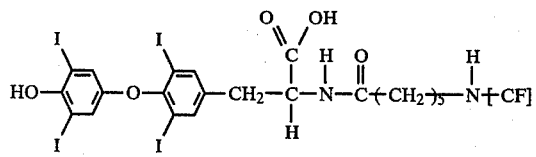

EXAMPLE 5

N-t-butoxycarbonylglycine (0.3 g:0.0017 mol) was treated with N,N'-dicyclohexylcarbodiimide (0.353 g:0.0017 mol) and N-hydroxysuccinimide (0.197 g:0.0017 mol) in 2 ml of N,N'-dimethylformamide. The reaction was allowed to proceed for 18 hours after which time the reaction mixture was diluted with 5 ml tetrahydrofuran, filtered, and the filtrate was concentrated under reduced pressure to yield N-t-butoxycarbonylglycine-N-hydroxysuccinimide ester as a white solid.

A portion of the N-t-butoxycarbonylglycine N-hydroxysuccinimide ester (0.35 g:0.003 mol) was treated with a solution containing L-thyroxine sodium salt pentahydrate (1.137 g:0.00128 mol) in methanol (20 ml) for 18 hours. The resulting mixture was passed through an ion exchange resin column of Bio-Rad AG® 50W-X8 (H+ form) with methanol and was concentrated under pressure to yield 1.0 g white solid.

A portion of the white solid (0.125 g:0.000134 mol) was reacted with trifluoroacetic acid (3.0 ml) for 30 minutes after which time the acid was removed via evaporation under reduced pressure and the resulting residue was dissolved in 1.5 ml N,N'-dimethylformamide and the pH of the resulting solution was made basic using triethylamine. To the resulting mixture was added 5-carboxyfluorescein N-hydroxysuccinimide ester (0.0075 g:0.000159 mol). The reaction was allowed to proceed for 18 hours, to yield a crude product which was purified using reverse phase thin-layer chromatography employing a methanol:water:acetic acid mixture (75:25:0.5) to yield a thyroxine-5-carboxyfluorescein conjugate as an orange solid having the formula:

Compound 4

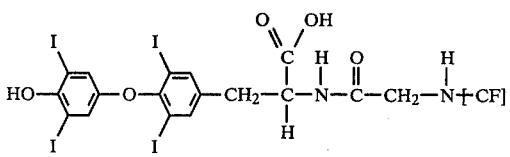

EXAMPLE 6

Gamma-aminobutyric acid (1.03 g:0.010 mol) and N-benzyloxycarbonyloxysuccinimide (2.49 g:0.01 mol) in N,N'-dimethylformamide (10 ml) was stirred for 18 hours at 22° C. The resulting clear solution was concentrated and the residue was treated with water. The resulting oil yielded white crystals which were then dried to yield a residue which was purified on a silica gel column employing dichloromethane:methanol mixture (95:5) as an eluent to yield gamma-(benzyloxycarbonylamino)butyric acid.

A portion of the gamma-(benzyloxycarbonylamino)butyric acid (0.237 g:0.001 mol) was treated with N,N'-dicyclohexylcarbodiimide (0.206 g:0.001 mol) and N-hydroxysuccinimide (0.135 g:0.0012 mol) in dichloromethane (2 ml) for two hours at 22° C. The reaction mixture was filtered and the filtrate was concentrated under reduced pressure to yield the succinimide ester of gamma(benzyloxycarbonylamino)butyric acid as an oily residue. The oily residue was reacted with L-thyroxine sodium salt pentahydrate (0.889 g,0.001 mol) in 5 ml of methanol for 18 hours. The reaction mixture was passed through an ion exchange resin column of Bio-Rad AG ® 50W-X8 (H+ form) with methanol and was evaporated to a glassy white solid which was purified using silica gel column chromatography employing a dichloromethane:methanol mixture (9:1) as the eluent to yield a white solid.

To a portion of the white solid (0.25 g:0.000025 mol) was added 0.4 ml of acetic acid containing 30% hydrobromic acid for 30 minutes. Upon addition of an excess diethylether, a hydrobromide salt precipitated which was washed, dried and then reacted with 5-carboxyfluorescein N-hydroxysuccinimide ester (0.25 g:0.00053 mol) in 0.4 ml of N,N'-dimethylformamide in the presence of triethylamine for a period of 16 hours to yield a product which was isolated as an orange solid using reverse phase thin-layer chromatography employing methanol:water:acetic acid mixture (70:30:0.5) to yield a thyroxine-5-carboxyfluorescein conjugate as an orange solid having the formula:

Compound 5

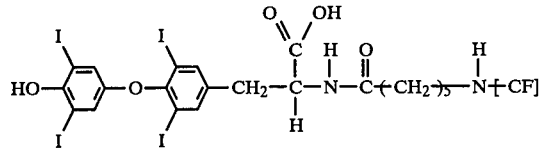

As previously mentioned, the tracers of the present invention are effective reagents for use in fluorescence polarization immunoassays. The following Examples illustrate the suitability of tracers of the present invention in immunoassays employing fluorescence polarization techniques. Such assays are conducted in accordance with the following general procedure:

(1) A measured volume of standard or test serum is delivered into a test tube and diluted with buffer;
(2) A known concentration of a tracer of the present invention optionally containing a surfactant is then added to each tube;
(3) A known concentration of antisera is added to the tubes;
(4) The reaction mixture is incubated at room temperature; and
(5) The amount of tracer bound to antibody is measured by fluorescence polarization techniques as a measure of the amount of ligand in the sample.

EXAMPLE 7

Thyroxine Assay

A. Materials required:
 (1) BGG buffer consisting of 0.1M sodium phosphate, pH 7.5, containing bovine gammaglobulin, 0.01% and sodium azide, 0.01%.
 (2) Tracer, consisting of thyroxine carboxyfluorescein derivative prepared in Example 2 at a concentration of approximately 60 nM in BGG buffer.
 (3) Antiserum, consisting of sheep antiserum raised against thyroxine, diluted appropriately in BGG buffer.
 (4) Samples of human serum or other biological fluid containing thyroxine.
 (5) Serum denaturing reagent—8M urea, 3% sodium dodecyl sulfate, 1% dithioerythritol, 50 mM ascorbic acid, 2 mM sodium editate in water.
 (6) Cuvettes, 10×75 mm glass culture tubes used as cuvettes.
 (7) Fluorometer capable of measuring fluorescence polarization with a precision of ±0.001 units.

B. Assay protocol:
 1. To 50 µl of serum denaturing reagent in a test tube was added 50 µl of a standard or unknown sample. The tubes containing the sample were capped and vortexed.
 2. A small volume of sample (20 microliters) is placed in each cuvette by pipetting 29 µl of denatured sample and diluting to 500 µl BGG buffer containing 25 ml pretreatment reagent and 25 ml antiserum in a dilution vessel. Next 175 µl of diluted sample is pipetted into the cuvette followed by 805 µl BGG buffer. Serum background fluorescence is read at this point.
 3. Tracer is added by pipetting, 0.75 µl diluted sample and 25 µl tracer and 780 µl BGG buffer into the cuvette.
 4. The contents of all cuvettes are well mixed and allowed to incubate for 4 minutes at 35° C. temperature.
 5. The fluorescence polarization is read on a fluorometer corrected for serum fluorescence background and a standard curve constructed to determine unknowns.

C. The results of a series of serum standards containing thyroxine at concentrations between 0 and 24 µg/dL are presented below. Each concentration was assayed in duplicate and averaged.

| Concentration of Thyroxine (µg/dL) | Polarization |
| --- | --- |
| 0 | .223 |
| 3 | .209 |
| 6 | .197 |
| 12 | .173 |
| 18 | .155 |
| 24 | .143 |

The polarization of fluorescence is seen to decrease in a regular manner as the thyroxine concentration increases, allowing construction of a standard curve. Unknown specimens treated in an identical manner can be quantitated by reference to the standard cruve.

Using the above method to analyze a patient's sera, the results obtained correlated with a radioimmunoassay method (Abbott's T4-PEG assay). A correlation coefficient of 0.0962 was obtained.

As evident from the above results, the tracers of the present invention are effective reagents in fluorescence polarization immunoassays. In addition to the properties mentioned above, the tracers of the present invention possess a high degree of thermal stability, a high degree of bound polarization, high quantum yields and are relatively easy to produce and purify.

In addition to being useful as reagents in a fluorescence polarization immunoassay, the thyroxine carboxyfluorescein derivatives of the present invention may be useful as tracers in a fluorescence polarization assay to determine unsaturated thyroxine binding protein sites ("T uptake") in accordance with the procedure of the following Example:

EXAMPLE 8

A. Reagents

1. Pretreatment Solution—A solution containing 0.15% sodium dodecyl sulfate 0.564M triethylenediamine (DABCO), and 0.1% sodium azide in 0.1M sodium phosphate buffer (pH 7.25).

2. $T_4$—Fluorescein Tracer—Consisting of Compound 4 prepared in Example 5 is employed at a concentration of $2.4 \times 10^{-7}$M in a buffered medium containing 0.005% sodium dodecyl sulfate, 0.1% bovine gamma globulin, and 0.1% sodium azide in 0.1M sodium phosphate buffer.

3. T Uptake Calibrators—Sheep anti-T antisera in a 4% human serum matrix having the following uptake values: 0, 0.5, 1.0, 1.5, 2.0, and 2.5. An uptake value of 1.0 is equivalent to the T uptake of normal serum.

4. Diluent buffer: 0.1M sodium phosphate containing 0.1% bovine gamma globulin and 0.1% sodium azide.

All polarized fluorescence measurements were made using a polarization spectrofluorimeter (Abbott $TD_x$ ™ Fluorescence Polarization Analyzer.

B. Assay Protocol

1. To 1 μl aliquot of an unknown sample is added 25 μl of the pretreatment solution and the resulting mixture is diluted to 1 ml with diluent buffer. The resultant assay solution is mixed and the polarized fluorescence background is measured.

2. To the assay solution in Step 1. is added a second 1 μl aliquot of the unknown sample, 25 μl of the pretreatment solution 25 μl of $T_4$ fluorescein tracer, and the buffer to a final volume of 2 ml. The resultant solution is mixed and the polarized fluorescence is measured.

3. The fluorescence polarization due to tracer binding is obtained by subtracting the polarized fluorescence intensities of the background from the final polarized fluorescence intensities of the mixture.

4. The polarization values obtained are proportional to the T uptake of each sample.

5. The fluorescence polarization for a sample is cmopared to a standard curve prepared using calibrators of known T uptake values to indicate the T uptake value.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula:

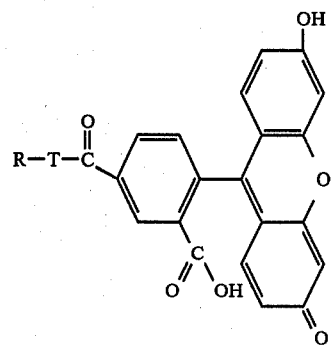

or

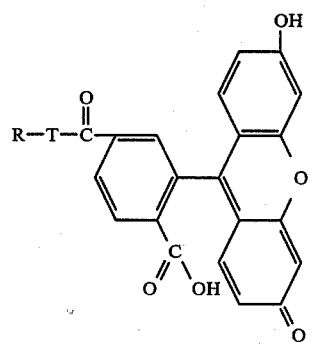

wherein

T is a

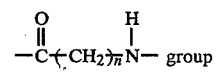 group wherein n is an integer of from 1 to 8; and

R is a ligand-analog having at least one common epitope with a ligand so as to be specifically recognizable by a common antibody;

and biologically acceptable salts thereof.

2. A compound according to claim 1 wherein R is a thyroxine analog.

3. A compound according to claim 2 wherein R is

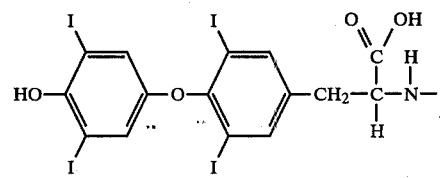

4. A compound according to claim 3 wherein n is an integer of from 2 to 4.

5. A compound according to claim 4 wherein n is 3.

6. A method for determining ligands in a sample comprising intermixing with said sample a tracer of the formula:

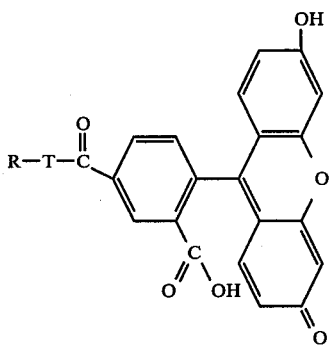

or

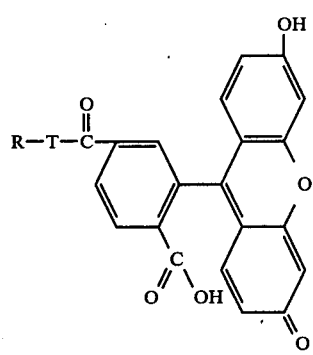

wherein
T is a

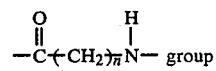 group wherein n is an integer of from 1 to 8; and,

R is a ligand-analog having at least one common epitope with a ligand so as to be specifically recognizable by a common antibody;

and biologically acceptable salts thereof; and an antibody capable of specifically recognizing said ligand and said tracer; and then determining the amount of tracer bound to antibody by fluorescence polarization techniques as a measure of the amount of ligand in the sample.

7. A method according to claim 6 wherein R" has a molecular weight within a range of 50 to 4000.

8. A method according to claim 7 wherein R is a thyroxine analog.

9. A method according to claim 8 wherein R is

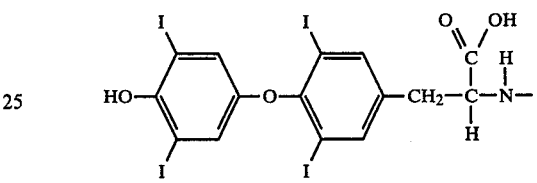

10. A method according to claim 6 or 9 wherein n is an integer of from 2 to 4.

11. A method according to claim 10 wherein n is 3.

* * * * *